United States Patent
Kanitz et al.

(10) Patent No.: US 8,937,175 B2
(45) Date of Patent: Jan. 20, 2015

(54) COMPOUNDS AS LIGANDS FOR TRANSITION METAL COMPLEXES AND MATERIALS MADE THEREOF, AND USE THEREFOR

(75) Inventors: Andreas Kanitz, Hoechstadt (DE); Daniel Stark, Marktzeuln (DE)

(73) Assignee: Osram GmbH, Munich (DE)

( * ) Notice: Subject to any disclaimer, the term of this patent is extended or adjusted under 35 U.S.C. 154(b) by 53 days.

(21) Appl. No.: 13/704,596

(22) PCT Filed: May 31, 2011

(86) PCT No.: PCT/EP2011/058903
§ 371 (c)(1),
(2), (4) Date: Mar. 1, 2013

(87) PCT Pub. No.: WO2011/157546
PCT Pub. Date: Dec. 22, 2011

(65) Prior Publication Data
US 2013/0158262 A1   Jun. 20, 2013

(30) Foreign Application Priority Data
Jun. 16, 2010   (DE) .................. 10 2010 023 959

(51) Int. Cl.
| | | |
|---|---|---|
| *C07D 253/10* | (2006.01) | |
| *C07D 233/54* | (2006.01) | |
| *C07F 15/00* | (2006.01) | |
| *C07F 13/00* | (2006.01) | |
| *C07D 253/08* | (2006.01) | |
| *C07D 401/04* | (2006.01) | |
| *C07D 403/04* | (2006.01) | |
| *C09K 11/06* | (2006.01) | |
| *H01L 51/00* | (2006.01) | |
| *H05B 33/14* | (2006.01) | |

(52) U.S. Cl.
CPC .......... *C07F 15/0033* (2013.01); *C07D 253/08* (2013.01); *C07D 401/04* (2013.01); *C07D 403/04* (2013.01); *C09K 11/06* (2013.01); *H01L 51/0085* (2013.01); *H05B 33/14* (2013.01); *C07D 253/10* (2013.01); *C09K 2211/1044* (2013.01); *C09K 2211/1059* (2013.01); *C09K 2211/185* (2013.01)
USPC ............... 544/183; 544/161; 257/40; 438/99; 430/58.5

(58) Field of Classification Search
CPC .... C07D 253/10; C07D 233/54; C07F 15/00; C07F 15/0033
USPC ....... 544/183, 181; 257/40; 438/99; 430/58.5
See application file for complete search history.

(56) References Cited

U.S. PATENT DOCUMENTS

| | | |
|---|---|---|
| 2011/0187265 A1 | 8/2011 | De Cola et al. |
| 2012/0169213 A1 | 7/2012 | De Cola et al. |
| 2013/0046096 A1 | 2/2013 | De Cola et al. |

FOREIGN PATENT DOCUMENTS

| | | |
|---|---|---|
| DE | 10 2009 031 683 A1 | 3/2011 |
| DE | 10 2010 005 632 A1 | 7/2011 |
| WO | WO 2010/007107 A1 | 1/2010 |

OTHER PUBLICATIONS

Khodja, M., et al., "Two-Step Syntheses of 3-Methyl and 3-Phenyl-1,2,4-Benzotriazines," Heteroatom Chemistry, vol. 17, No. 2, 2006, pp. 166-172.
Al-Awadi, H., et al., "Gas-phase thermolysis of condensed—1,2,4-triazines: interesting routes toward heterocyclic ring systems," Elsevier Ltd., Tetrahedron, vol. 63, Issue 52, Dec. 24, 2007, pp. 12948-12953.
Goerner, H., et al., "Photoreduction of electron-deficient azaarenes by di- and trialkylamines," Journal of Chemical Society, Perkin Transactions 2, Issue 8, Jul. 17, 2000, pp. 1723-1733.

*Primary Examiner* — Venkataraman Balasubramanian
(74) *Attorney, Agent, or Firm* — Slater & Matsil, L.L.P.

(57) ABSTRACT

The invention relates to novel compounds as ligands for transition metal complexes and materials made thereof that can be used, for example, as emitters in organic light-emitting electrochemical cells (OLEECs). According to the invention, non-fluorinated electron-poor emitter materials are disclosed for the first time that can be used in organic light-emitting electrochemical cells.

8 Claims, No Drawings

COMPOUNDS AS LIGANDS FOR TRANSITION METAL COMPLEXES AND MATERIALS MADE THEREOF, AND USE THEREFOR

This patent application is a national phase filing under section 371 of PCT/EP2011/058903, filed May 31, 2011, which claims the priority of German patent application 10 2010 023 959.3, filed Jun. 16, 2010, each of which is incorporated herein by reference in its entirety.

TECHNICAL FIELD

The invention relates to novel compounds as ligands for transition metal complexes and to materials produced therefrom, which can be used, for example, as emitters in organic light-emitting electrochemical cells (OLEECs).

BACKGROUND

OLEECs have been developed in the last few years and have the potential to attain the performance of, and be producible even less expensively than, the organic electroluminescent diodes (OLEDs).

WO 2010/007107, DE 10 2009 031 683 and DE 10 2010 005 632 have already disclosed transition metal complexes as emitting materials for these components.

DETAILED DESCRIPTION OF ILLUSTRATIVE EMBODIMENTS

A particular problem is still that of stable OLEEC emitters which emit at short wavelengths, i.e., in the blue. Such blue OLEEC emitters have to date been obtained only on the basis of fluorinated ligands, the aromatic base structure of which is particularly electron-deficient as a result of the fluorine substitution. However, the stability of such materials in the component is only very low. The emission wavelength shifts to a longer-wave spectral region within a short time, which suggests exchange of the fluorine in the electrical field.

In contrast OLEEC emitters without fluorinated ligand systems are very long-lived, but do not emit in the blue.

In one aspect, the invention provides novel ligand systems which, without fluorination, lead to a similarly low electron density in the aromatic base structure and therefore lead to the same effect of a short-wave, blue luminescence.

The invention provides the novel substance class of the electron-deficient heterocycles of the 3-arylbenzo-1,2,4-triazine series A

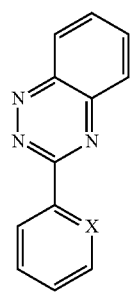

where X is —CH= and —N= and the ortho positions of the adjacent phenyl rings may be joined to one another by a chemical bond.

The invention also provides a novel class of cationic transition complexes with a ligand A, for example a combination of ligand A with 2-phenylimidazole ligand structures B or with itself,

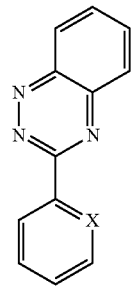

A

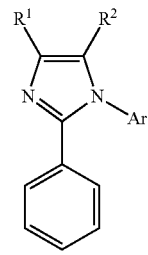

B where, in structure A, X is —CH= and —N= and, in the structure B, Ar is "phenyl" or "2,6-diisopropyl-1-phenyl," the ortho positions of the adjacent phenyl rings may be joined to one another by a chemical bond, R1 and R2 may each independently be "H" or "phenyl" and together form a annulated benzene ring.

Finally, the invention provides for the use of a transition metal complex with a ligand A or for the use of a combination of a ligand A with a ligand B in an organic light-emitting electrochemical cell.

The following reaction scheme depicts a preferred preparation of the novel OLEEC emitters by the Nonoyama synthesis route.

1.) Reaction scheme for complex formation:

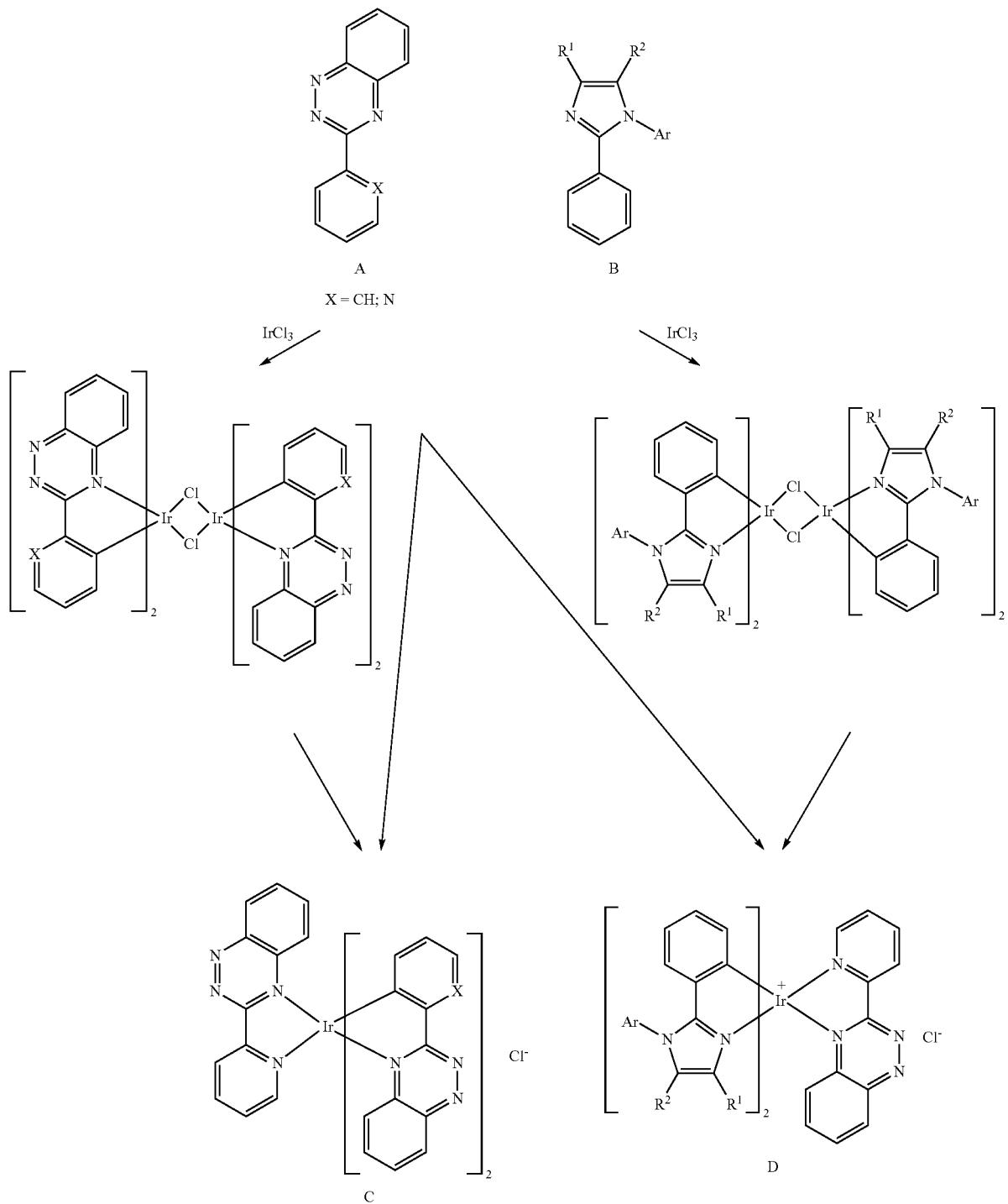

Access to cationic iridium complexes by the Nonoyama route has been known from the literature for a few years.

Unknown to date are all structures which can be formed by the incorporation of the A ligand.

These inventive structures C and D are blue-emitting materials which have to be provided with a suitable anion by salt exchange for use in an OLEEC device. Tetrafluoroborate, hexafluorophosphate and hexafluoroantimonate are particularly suitable anions. Likewise suitable are anions of ionic liquids, the organo component of which corresponds to the anion.

For formation of the transition metal complex, for example, iridium is used, but it is also possible to use other transition metal atoms such as ruthenium, rhodium, palladium, rhenium, osmium, platinum, gold and the lanthanides as the central atom according to the invention.

The preparation of the ligand A is accomplished according to reaction scheme 2.

2-Nitrophenyl hydrazine is converted to an amidrazone by reaction with imido esters, and these are hydrogenated over a platinum catalyst and filtered off from the catalyst. The reduction product which has been freed of the solvent is stirred with silylated polyphosphoric acid.

2.) Reaction scheme for ligand system A

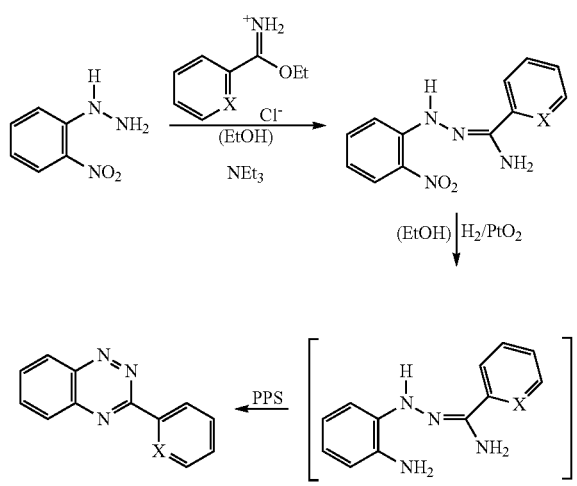

Working examples will now be described.

Preparation of N'-(2-nitrophenyl)picoline hydrazonamide 16 g (0.104 mol; 1 equivalent) of 2-nitrophenyl hydrazine and 15.55 g (0.104 mol; 1 equivalent) of picolinimidic acid ethyl ester are initially charged in 200 ml of THF. The mixture is then heated to 50° C. for six hours. On completion of reaction, a dark solid precipitates out. A check by thin-film chromatography (absorbent: silica gel 60; eluent: 4:1 toluene/ethyl acetate) shows virtually complete conversion. The solvent is removed on a rotary evaporator, and the remaining precipitate is recrystallized from a little ethanol. The solid is filtered off with suction and washed with a little cold ethanol. Yield: 24.2 g (90%); dark green, sparkling powder M=257.25 g/mol (C12H11N5O2) Melting point: 197° C. MS (ESI): m/z=258.3 ([M+H]$^+$).

Preparation of N'-(2-nitrophenyl)benzohydrazonamide 10 g (0.065 mol; 1 equivalent) of 2-nitrophenyl hydrazine and 12.07 g (0.065 mol; 1 equivalent) of benzoimidic acid ethyl ester hydrochloride are initially charged in 200 ml of a mixture of anhydrous ethanol and THF in a ratio of 1:1 and 6.58 g (0.065 mol; 1 equivalent) of triethylamine are added. The mixture is boiled at reflux for two hours. After cooling the reaction mixture, a dark red solid precipitates out, which is filtered off with suction and washed with cold ethanol. The melting point is determined to be 180-182° C. Yield: 6.8 g (41%); dark red, amorphous powder M=256.26 g/mol (C13H12N4O2) MS (ESI): m/z=257.3 ([M+H]$^+$).

Preparation of 3-(pyridin-2-yl)benzo[e][1,2,4]-triazine by reduction of N'-(2-nitrophenyl)picoline hydrazonamide by means of hydrogen over a platinum catalyst. The reduction of the amidrazone is conducted in a hydrogenation apparatus. 8 g (0.0311 mol) of N'-(2-nitrophenyl)picolinohydrazonamide are initially charged in 500 ml of ethanol in a 1000 ml Erlenmeyer flask. A catalytic amount of platinum(IV) oxide is added to this suspension. Once the Erlenmeyer flask has been installed into the hydrogenation apparatus, the required volume of hydrogen is introduced into the apparatus and the reduction of the amidrazone present is conducted with vigorous stirring. After the reduction has ended, the elemental platinum is filtered off and the filtrate is very substantially concentrated.

The oily mass formed is weighed, 60 ml of a solution of trimethylsilyl polyphosphate (preparation as described below) are added, and the mixture is boiled at reflux for one hour. The reaction mixture is then concentrated again as far as possible and a few milliliters of water are added. The pale yellow solid which then crystallizes out gradually is recrystallized from ethanol and then filtered off with suction; this leaves a white precipitate. Yield: 1.61 g (25%); white, fine pulverulent precipitate M=208.22 g/mol (C12H8N4) Melting point: 145° C. MS (EI): m/z=208 ([M]$^+$).

Preparation of trimethylsilyl polyphosphate: In a flask with a reflux condenser and drying tube, 11.37 g (0.070 mol; 1 equivalent) of hexamethyldisiloxane and 10 g (0.070 mol; 1 equivalent) of phosphorus pentoxide, P2O5, are heated at reflux in 100 ml of 1,2-dichloroethane for about two hours, until all P2O5 has dissolved.

Preparation of a di-μ-chloro complex of B A 500 ml one-neck flask is initially charged under inert conditions with 0.69 g (2.3 mmol; 1 equivalent) of iridium(III) chloride hydrate, IrCl3*nH2O, and 0.40 g (6.9 mmol; 3 equivalents) of sodium chloride, NaCl, in 20 ml of degassed water, and 1.76 g (4.6 mmol; 2 equivalents) of 1-(2,6-diisopropylphenyl)-2-phenyl-1H-imidazole which has been dissolved in a mixture of 12 ml of degassed water and 28 ml of 2-ethoxyethanol are added. The mixture is heated to about 50° C. and, after 3 hours, by TLC monitoring (absorbent: silica gel 60; eluent: 9:1 toluene/acetone), substantial conversion to the complex is observed. 200 ml of diethyl ether and 20 ml of methanol are added, and the yellow-green solid formed is filtered off with suction and washed with methanol. The compound can be obtained with a yield of 32% and decomposes above 310° C. Yield: 0.54 g (32%); pale yellow-green precipitate M=1669.02 g/mol (C84H92Cl2Ir2N8) Melting point: >310° C. (decomposition) MS (ESI): m/z=799.4 ([(M/2)-Cl]$^+$).

Preparation of the iridium coordination compound from A (X═N) and B (di-μ-chloro complex 0.50 g (0.30 mmol; 1 equivalent) of B (di-μ-chloro complex) is initially charged in 30 ml of chloroform. 0.12 g (0.60 mmol; 2 equivalents) of 3-(pyridin-2-yl)benzo[e][1,2,4]triazine A (X═N) is added to the resulting suspension. The mixture is boiled at reflux for about 30 minutes. The precipitated pale yellow solid is filtered off with suction and washed with diethyl ether. The yield is 90%. The melting point is 194° C.; the material decomposes at the same time. Yield: 0.56 g (90%); yellow solid. M=787.29 g/mol (C35H25ClIrN7O) Emission maximum (PL): $\lambda_{max}$=484 nm (acetonitrile).

The present invention for the first time presents unfluorinated electron-deficient emitter materials which can be used in organic light-emitting electrochemical cells.

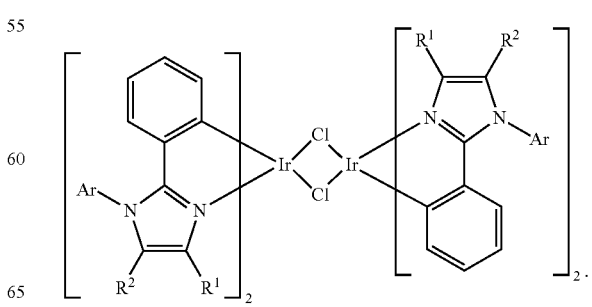

8. A cationic transition complex according to claim 2, which comprising the following compound:
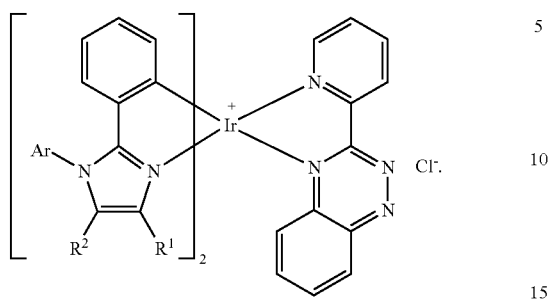

The invention claimed is:

1. A cationic transition complex comprising a central atom and two ligands A according to the following structural formulae

A

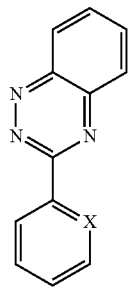

A

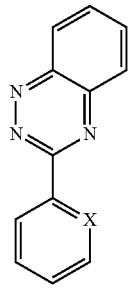

where X is —CH= and/or —N=; and
wherein the central atom comprises an atom selected from the group consisting of iridium, ruthenium, rhodium, palladium, rhenium, osmium, platinum, gold and the lanthanides.

2. A cationic transition complex comprising:
a central atom,
a ligand A, and
a 2-phenylimidazole ligand structure B,

A

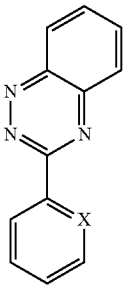

B

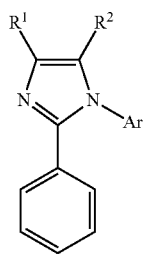

where, in structure A, X is —CH= and —N= and, in the structure B, Ar is "phenyl" or "2,6-diisopropyl-1-phenyl,"
wherein R1 and R2 may each independently be "H" or "phenyl" and together form a annulated benzene ring, and
wherein the central atom comprises an atom selected from the group consisting of iridium, ruthenium, rhodium, palladium, rhenium, osmium, platinum, gold and the lanthanides.

3. A material for a light-emitting layer of an organic light-emitting electrochemical cell comprising a cationic transition complex according to claim 1.

4. A material for a light-emitting layer of an organic light-emitting electrochemical cell, comprising a transition metal complex with a ligand A in combination with a ligand B according to claim 2.

5. A cationic transition complex according to claim 1, which comprising the following compound:

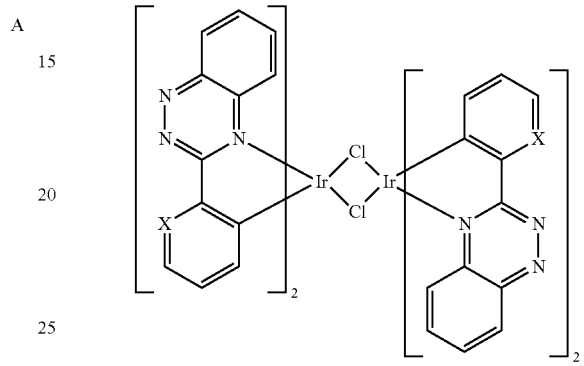

where X is —CH= and/or —N=.

6. A cationic transition complex according to claim 1, which comprising the following compound:

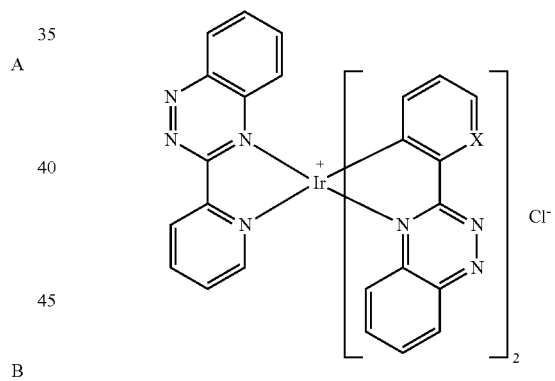

where X is —CH= and/or —N=.

7. A cationic transition complex, which comprising the following compound: